United States Patent [19]

Schriewer et al.

[11] Patent Number: 5,051,418
[45] Date of Patent: Sep. 24, 1991

[54] ANTIBACTERIAL 8-CYANO-1-CYCLOPROPYL-1,4-DIHYDRO-4-OXO-3-QUINOLINECARBOXYLIC ACIDS

[75] Inventors: Michael Schriewer; Klaus Grohe, both of Odenthal; Uwe Petersen, Leverkusen; Ingo Haller, Wuppertal; Karl G. Metzger, Wuppertal; Rainer Endermann, Wuppertal; Hans-Joachim Zeiler, Velbert, all of Fed. Rep. of Germany

[73] Assignee: Bayer Aktiengesellschaft, Leverkusen, Fed. Rep. of Germany

[21] Appl. No.: 434,666

[22] Filed: Nov. 13, 1989

Related U.S. Application Data

[62] Division of Ser. No. 144,884, Jan. 14, 1988, Pat. No. 4,908,366.

[30] Foreign Application Priority Data

Jan. 28, 1987 [DE] Fed. Rep. of Germany ....... 3702393

[51] Int. Cl.⁵ ..................... A61K 31/54; C07D 417/04
[52] U.S. Cl. .............................. 514/228.2; 514/226.8; 544/54; 544/58.2; 544/58.6; 544/128; 544/363; 544/349; 546/156
[58] Field of Search ...................... 544/58.2, 58.6, 54, 544/226.8; 514/228.2

[56] References Cited

U.S. PATENT DOCUMENTS 4,894,458  1/1990  Masuzawa et al. .............. 544/58.6
4,908,366  3/1990  Schriewer et al. ............... 544/58.2

Primary Examiner—C. Warren Ivy
Assistant Examiner—James H. Turnipseed
Attorney, Agent, or Firm—Sprung Horn Kramer & Woods

[57] ABSTRACT

Antibacterial 8-cyano-1-cyclopropyl-1,4-dihydro-4-oxo-3-quinolinecarboxylic acid derivatives of the formula

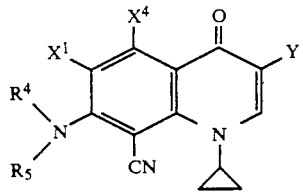

in which
Y represents a carboxyl group, a nitrile group, an ester group —COOR$^1$ or an acid amide group —CONR$^2$R$^3$,
X$^1$ represents hydrogen nitro, alkyl or halogen
X$^4$ can be hydrogen or halogen, or alkyl,
R$^4$ and R$^5$, together with the nitrogen atom to which they are bonded, form a 5- or 6-membered heterocyclic ring which can additionally contain the atoms or groups —O—, —S—, —SO—, —SO$_2$—,

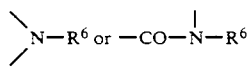

as ring members or the group

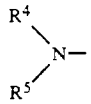

can also represent a ring system of the structure

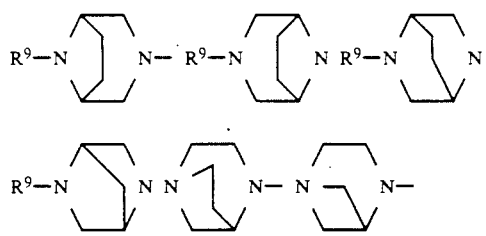

which can optionally be substituted on the ring carbons by methyl and pharmaceutically usable hydrates, salts or esters thereof.

These compounds have a high antibacterial activity and are therefore suitable as active compounds for human and veterinary medicine.

6 Claims, No Drawings

ANTIBACTERIAL 8-CYANO-1-CYCLOPROPYL-1,4-DIHYDRO-4-OXO-3-QUINOLINECARBOXYLIC ACIDS

This is a division of application Ser. No. 144,884 filed 1-14-88 now U.S. Pat. No. 4,908,366.

The present invention relates to new 8-cyano-1-cyclopropyl-1,4-dihydro-4-oxo-3-quinolinecarboxylic acid derivatives, processes for their preparation and antibacterial agents containing these compounds.

The new 8-cyano-1-cyclopropyl-1,4-dihydro-4-oxo-3-quinolinecarboxylic acid derivatives of the formula I

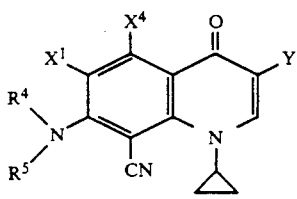
(I)

in which

Y represents a carboxyl group, a nitrile group, an ester group —COOR$^1$ or an acid amide group —CONR$^2$R$^3$, wherein R$^1$ represents alkyl, preferably C$_1$-C$_4$-alkyl and R$^2$ and R$^3$ independently of one another represent hydrogen or alkyl, preferably C$_1$-C$_4$-alkyl, and R$^3$ can also be optionally substituted phenyl, X$^1$ represents hydrogen, nitro, alkyl, preferably with 1-3 carbon atoms, or halogen, preferably fluorine, X$^4$ can be hydrogen or halogen, preferably Cl or F, or alkyl, preferably with 1-3 C atoms, in particular methyl, R$^4$ and R$^5$, together with the nitrogen atom to which they are bonded, form a 5- or 6-membered heterocyclic ring which can additionally contain the atoms or groups —O—, —S—, —SO—, —SO$_2$—,

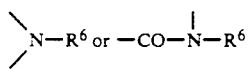

as ring members and which can optionally be mono-, di- or trisubstituted on the carbon atoms by identical or different substituents from the group comprising C$_1$-C$_4$-alkyl, phenyl and cyclohexyl which are optionally mono-, di- or trisubstituted by chlorine, fluorine, bromine, methyl, phenyl, hydroxyl, methoxy, benzyloxy, nitro or piperidino, 2-thienyl, hydroxyl, alkoxy with one to three carbon atoms, amino, methylamino, ethylamino, aminomethyl, methylaminomethyl and ethylaminomethyl, wherein R$^6$ represents hydrogen, a branched or straight-chain alkyl, alkenyl or alkynyl group which has 1 to 6 carbon atoms and can optionally be substituted by one or two hydroxyl, alkoxy, alkylamino or dialkylamino groups with in each case 1 to 3 carbon atoms for an alkyl radical, the cyano group, the alkoxycarbonyl group with 1 to 4 carbon atoms in the alcohol part, a phenylalkyl group which is optionally substituted in the phenyl radical and has up to 4 carbon atoms in the aliphatic part, a phenacyl radical which is optionally mono- or disubstituted by hydroxyl, methoxy, chlorine or fluorine, or an oxoalkyl radical with up to 6 carbon atoms, or furthermore denotes a radical COR$^7$ or SO$_2$R$^8$, wherein R$^7$ represents hydrogen, straight-chain or branched alkyl which has 1 to 4 carbon atoms and is optionally substituted by 1 or 2 substituents from the series comprising amino, alkoxycarbonyl with 1 to 3 carbon atoms in the alkyl part, carboxyl, alkoxy with 1 to 3 carbon atoms and halogen, such as chlorine, bromine or fluorine, or represents amino, alkylamino or dialkylamino with 1 to 5 carbon atoms in the alkyl part, and R$^8$ represents straight-chain or branched alkyl with 1 to 3 carbon atoms, or the group

can also represent a ring system of the structure

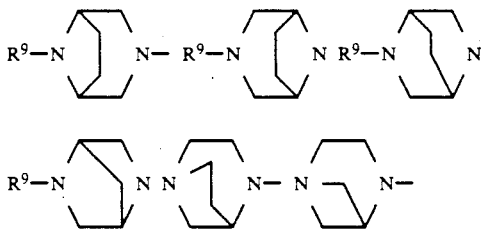

which can optionally be substituted on the ring carbons by methyl, wherein

R$^9$ can represent hydrogen, methyl, ethyl, hydroxyethyl, benzyl or p-aminobenzyl, and pharmaceutically usable hydrates or salts thereof, preferably alkali metal, alkaline earth metal, silver and guanidinium salts, and their esters.

The compounds have a high antibacterial activity. They are therefore suitable as active compounds for human and veterinary medicine. They can also be used as intermediate products for the preparation of other bactericides.

Preferred compounds of the formula (I) are those in which

Y represents a carboxyl group, a nitrile group or an ester group —COOR$^1$, wherein R$^1$ is methyl or ethyl, X$^1$ represents fluorine, X$^4$ represents hydrogen, R$^4$ and R$^5$, together with the nitrogen atom to which they are bonded, can form a 5- or 6-membered heterocyclic ring which can additionally contain an oxygen atom or the groups

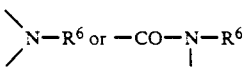

as a ring member and can optionally be mono- or disubstituted on the carbon atoms by C$_1$-C$_2$-alkyl, cyclohexyl, phenyl which is optionally substituted by chlorine, fluorine, methyl, phenyl, hydroxyl, methoxy, benzyloxy, nitro or piperidino, 2-thienyl or hydroxyl, wherein $R^6$ represents hydrogen, a branched or straight-chain alkyl group which has 1 to 3 carbon atoms and can optionally be substituted by one or two hydroxyl groups, a phenacyl radical, an oxalkyl radical with up to 4 carbon atoms or a radical $COR^7$,
wherein $R^7$ denotes hydrogen or alkyl with one or two carbon atoms, or the group $$\begin{array}{c} R^4 \\ \diagdown \\ N- \\ \diagup \\ R^5 \end{array}$$

can also represent a ring system of the structure $R^9-N\underset{\diagdown\diagup}{\overset{\diagup\diagdown}{\bigcirc}}N-$  $R^9-N\underset{\diagdown\diagup}{\overset{\diagup\diagdown}{\bigcirc}}N$  $R^9-N\underset{\diagdown\diagup}{\overset{\diagup\diagdown}{\bigcirc}}N$ $N\underset{\diagdown\diagup}{\overset{\diagup\diagdown}{\bigcirc}}N-$  $R^9-N\underset{\diagdown\diagup}{\overset{\diagup\diagdown}{\bigcirc}}N-$  $N\underset{\diagdown\diagup}{\overset{\diagup\diagdown}{\bigcirc}}N-$ wherein $R^9$ can represent hydrogen or methyl.

Particularly preferred compounds of the formula I are those in which

Y represents a carboxyl group, $X^1$ represents fluorine, $X^4$ represents hydrogen, $R^4$ and $R^5$, together with the nitrogen atom to which they are bonded, can form a 5- or 6-membered heterocyclic ring which can additionally contain an oxygen atom or the groups $$\diagdown\!\!N\!-\!R^6 \quad or \quad -CO\!-\!\underset{|}{N}\!-\!R^6$$

as a ring member and can optionally be mono- or disubstituted on the carbon atoms by $C_1$-$C_2$-alkyl, cyclohexyl, phenyl which is optionally substituted by chlorine, fluorine, methyl, phenyl, hydroxyl, methoxy, benzyloxy, nitro or piperidino, 2-thienyl or hydroxyl,
wherein $R^6$ represents hydrogen, a straight-chain or branched alkyl group which has 1 to 3 carbon atoms and can optionally be substituted by one or two hydroxyl groups, a phenacyl radical, an oxalkyl radical with up to 4 carbon atoms or a radical $COR^7$,
wherein $R^7$ denotes hydrogen or alkyl with one or two carbon atoms.

The compounds of the formula I according to the invention are obtained by a process in which quinolone-carboxylic acid derivatives of the formula (II)

(II)

in which the radicals $X^1$, $X^4$ and Y have the abovementioned meanings and $X^2$ represents halogen, preferably chlorine or fluorine, are reacted with amines of the formula III $$\begin{array}{c} R^4 \\ \diagdown \\ NH \\ \diagup \\ R^5 \end{array} \quad (III)$$

in which $R^4$ and $R^5$ have the abovementioned meanings, if appropriate in the presence of acid-binding agents (Method A).

This process does not necessarily have to be carried out such that $R^4$ and $R^5$ in the amines of the formula (III) already have the final meaning which they have in the compounds of the formula (I) according to the invention. On the contrary, it is also possible to use precursors to the radicals $R^4$ and $R^5$ in a first step and then to convert these into the final form of $R^4$ and $R^5$ in one or more subsequent reaction steps.

Thus, for example, compounds of the formula (I) according to the invention can be obtained by a process in which a 7-(1-piperazinyl) compound of the formula (IV)

(IV)

in which $X^1$, $X^4$ and Y have the abovementioned meanings and the piperazinyl radical can be substituted on the carbon atoms in the manner described for $R^4$ and $R^5$, for example by 1, 2 or 3 radicals from the group comprising $C_1$-$C_4$-alkyl, 2-thienyl and optionally substituted cyclohexyl or phenyl, is reacted with compounds of the formula (V)

$R^6X$     (V)

in which $R^6$ has the abovementioned meaning but cannot be hydrogen and

X denotes fluorine, chlorine, bromine, iodine, hydroxy, acyloxy, ethoxy, phenoxy or 4-nitrophenoxy, if appropriate in the presence of acid-binding agents (Method B)

In this reaction procedure, the piperazinyl radical in the 7-position can thus be introduced in a first reaction step by the method first mentioned—which leads to the compound (IV) which is already according to the invention—and other desired substituents can then be introduced, in this case, for example R⁶, in a subsequent step.

In another embodiment of the process according to the invention, compounds of the formula (I) according to the invention are obtained, for example, by a process in which 7-(1-piperazinyl)quinolonecarboxylic acid derivatives of the formula (IV) in which the piperazinyl radical can be substituted on the carbon atoms in the manner already described, for example by 1, 2 or 3 constituents from the group comprising $C_1$-$C_4$-alkyl, 2-thienyl and optionally substituted cyclohexyl or phenyl, are reacted with Michael acceptors of the formula (VI)

B—CH=CH₂     (VI)

in which
B represents CN, CO-R¹⁰ or COOR¹¹,
wherein
R¹⁰ represents methyl or ethyl and
R¹¹ represents methyl, ethyl or n- or i-propyl (Method C).

If, for example, 1-methylpiperazine and 7-chloro-8-cyano-1-cyclopropyl-6-fluoro-1,4-dihydro-4-oxo-3-quinolinecarboxylic acid are used as starting substances in the reaction according to the method first mentioned, the course of the reaction can be represented by the following equation:

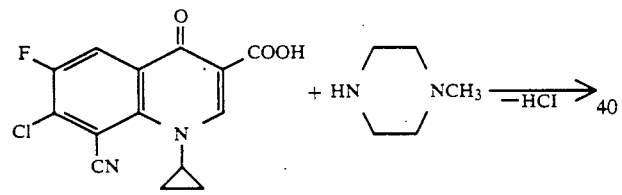

If, for example, ethyliodide and 8-cyano-1-cyclopropyl-6-fluoro-1,4-dihydro-4-oxo-7(1-piperazinyl)-3-quinolinecarboxylic acid are used as starting substances in the reaction according to the modified method, the course of the reaction can be represented by the following equation:

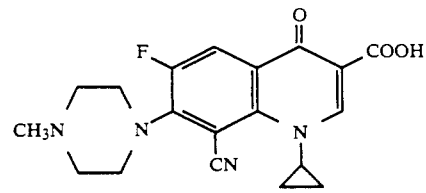

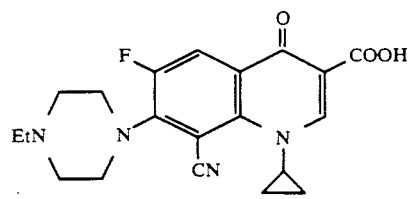

The reaction with Michael acceptors with, for example, 8-cyano-1-cyclopropyl-6-fluoro-1,4-dihydro-4-oxo-7-(1-piperazinyl)-3-quinolinecarboxylic acid and methylvinylketone as starting substances can be represented by the following equation:

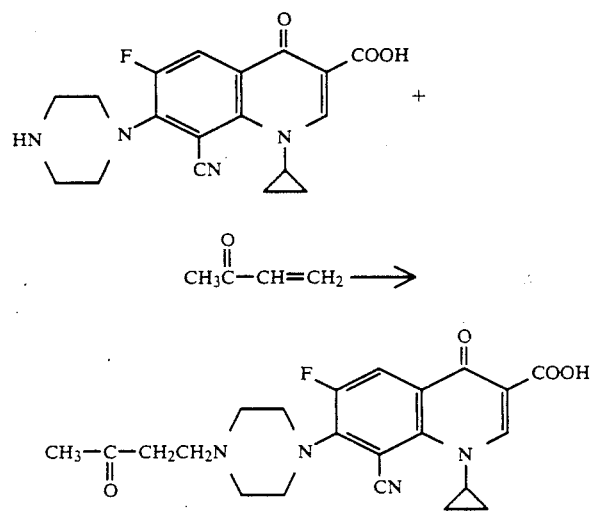

The quinolonecarboxylic acids of the formula (II) which can be used as starting substances in the process according to the invention can be prepared in accordance with the following equation (Process 1).

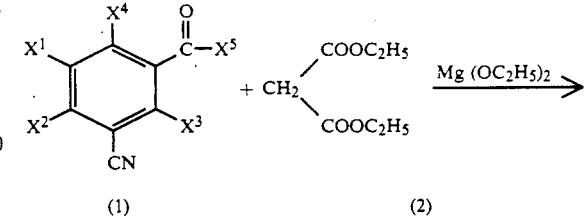

X³=F, Cl, NO₂
X¹, X², X⁴ as mentioned above
X⁵=Cl, Br, F

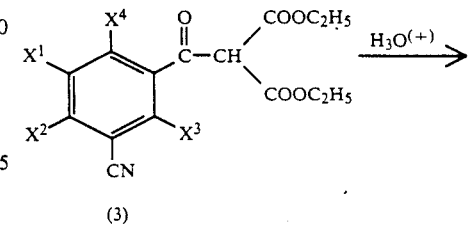

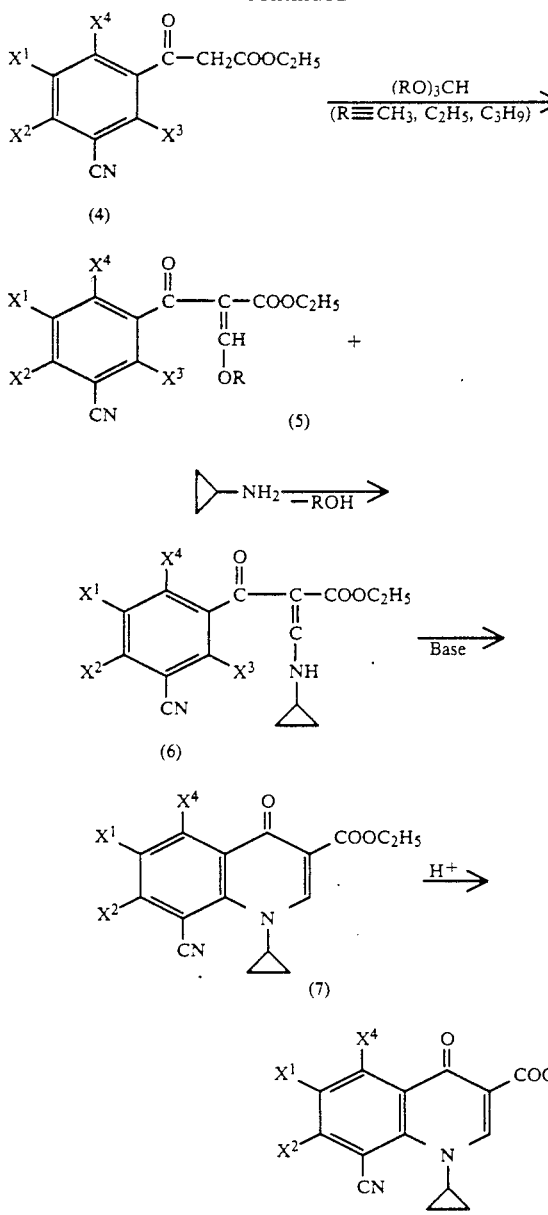

(4)

(5)

(6)

(7)

(II)

According to this equation, diethyl malonate (2) is acylated with the corresponding benzoyl fluoride or chloride (1) in the presence of magnesium ethylate to give the benzoyl malonate (3) (Organicum, 3rd edition 1964, page 438).

Partial hydrolysis and decarboxylation of (3) in an aqueous medium with catalytic amounts of sulphuric acid or p-toluenesulphonic acid gives a good yield of the ethyl benzoylacetate (4), which is converted into the ethyl 3-ethoxyacrylate (5) with triethyl orthoformate/acetic anhydride. The reaction of (5) with cyclopropylamine in a solvent, such as, for example methylene chloride, alcohol, chloroform, cyclohexane or toluene, leads to the desired intermediate product (6) in a slightly exothermic reaction.

The cyclization reactions (6)→(7) are carried out in a temperature range from about 60° to 300° C., preferably 80° to 180° C.

Diluents which can be used are dioxane, dimethyl sulphoxide, N-methylpyrrolidone, sulpholane, hexamethylphosphoric acid triamide and, preferably, N,N-dimethylformamide.

Possible acid-binding agents for this reaction stage are potassium tert.-butanolate, butyl-lithium, lithium-phenyl, phenylmagnesium bromide, sodium methylate, sodium hydride and sodium or potassium carbonate, and particularly preferably potassium fluoride or sodium fluoride. It may be beneficial to use an excess of 10 mol % of base.

The hydrolysis of the esters (7) carried out in the last step to give the corresponding carboxylic acids can be effected under the customary acid or basic conditions.

The 2,4-dichloro-3-cyano-5-fluorobenzol chloride used as the starting substance for this synthesis route is obtainable as follows:

a) 2,4-dichloro-5-fluoro-3-nitro-benzoic acid 40 ml of concentrated nitric acid are added dropwise to 34 ml of concentrated sulphuric acid, while cooling with ice and stirring. 20.9 g of 2,4-dichloro-5-fluorobenzoic acid are introduced in portions into this nitrating mixture, whereupon the temperature rises to 45°–50° C. The mixture is then heated at 90°–100° C. for a further 3 hours, the mixture is cooled to room temperature and poured onto 350 ml of ice-water and the precipitate is filtered off with suction and washed with water. The moist crude product is dissolved in 30 ml of hot methanol and 150 ml of $H_2O$ are added to the solution. The precipitate is filtered off cold with suction, washed with $CH_3OH/H_2O$ and dried in vacuo at 80° C. 21.2 g of crude 2,4-dichloro-5-fluoro-3-nitro-benzoic acid are obtained. It is sufficiently pure for further reactions. Melting point: 192° C. (from toluene/petroleum ether).

b) 3-Amino-2,4-dichloro-5-fluoro-benzoic acid 254 g (1 mol) of 2,4-dichloro-5-fluoro-3-nitro-benzoic acid are hydrogenated in 1.8 l of ethanol in the presence of 60 g of Raney nickel at 11°–20° C. under 10 bar of hydrogen, the mixture is filtered and the filtrate is concentrated in vacuo. The paste-like residue is kneaded with water and the product which has crystallized out is filtered off with suction, washed with water and dried.

Yield: 197 g (88% of theory)

Melting point: 175°–177° C., from toluene: 184°–187° C.

c) 2,4-Dichloro-3-cyano-5-fluoro-benzoic acid 56 g of 3-amino-2,4-dichloro-5-fluoro-benzoic acid are diazotized in 700 ml of half-concentrated sulphuric acid by addition of 2.5 molar $NaNO_2$ solution at 0°–5° C. Excess nitrite is destroyed by addition of urea. The diazonium salt solution is then added dropwise to a mixture of 27 g of CuCN and 200 ml of 4.5 molar NaCN solution at 0° C. After the end of the dropwise addition, the mixture is heated at 80° C. for one hour. It is then cooled and the solid is isolated and dried. The solid (64.3 g) is boiled up with toluene. The insoluble material is filtered off and the solvent is largely evaporated off. On cooling, the acid crystallizes out.

Yield: 44 g

Melting point: 188°–190° C.; recrystallization again from toluene gives a melting point of 203°–205° C.

d) 2,4-Dichloro-3-cyano-5-fluoro-benzoic acid chloride 25 g of 2,4-dichloro-3-cyano-5-fluoro-benzoic acid and 30 ml of thionyl chloride are boiled until the evolution of gas has ended. The excess thionyl chloride is then stripped off in vacuo. 25.6 g of acid chloride of melting point 69°–72° C. remain.

The amines (III) used as starting substances are known or can be obtained by processes which are known from the literature, U.S. Pat. No. 4,166,188 and J. Med. Chem. 26, 1116 (1983). The corresponding 2-cyclohexylpiperazines are obtained from the 2-arylpiperazines by catalytic hydrogenation: for example 2-cyclohexylpiperazine (waxy, melting point 71°–73° C.). Examples which may be mentioned are: morpholine, piperidine, thiomorpholine, pyrrolidone, piperazine, N-methylpiperazine, N-ethylpiperazine, N-(2-hydroxyethyl)-piperazine, N-formylpiperazine, 2-methylpiperazine, 1,2-dimethylpiperazine, cis- and trans-2,5-dimethylpiperazine, 2-propylpiperazine, 2-isopropylpiperazine, 2-isobutylpiperazine, 2-piperazinone, 1-methyl-2-piperazinone, 1-ethyl-2-piperazinone, 2-cyclohexyl-1-piperazine, 2-phenylpiperazine, 2-(4-chlorophenyl)-piperazine, 2-(4-fluorophenyl)-piperazine, 2-(4-bromophenyl)-piperazine, 2-(4-methylphenyl)-piperazine, 2-(4-biphenyl)-piperazine, 2-(4-methoxyphenyl)-piperazine, 2-(4-benzyloxyphenyl)-piperazine, 2-(4-hydroxyphenyl)-piperazine, 2-(4-nitrophenyl)-piperazine, 2-(3-nitrophenyl)-piperazine, 2-(4-piperidinophenyl)-piperazine, 2-(3,4-dimethoxyphenyl)-piperazine, 2-(3,4,5-trimethoxyphenyl)-piperazine, 2-(3-dimethoxy-6-methyl)-piperazine, 2-(2-thienyl)-piperazine, 3-aminopyrrolidine, 2,5-diazabicyclo[2.2.1]heptane dihydrochloride, 2-methyl-2,5-diazabicyclo[2.2.1]heptane dihydrochloride, 8-methyl-3,8-diazabicyclo[3.2.1]octane dihydrochloride, 3-methyl-3,8-diazabicyclo[3.2.1]octane dihydrochloride, 3-(4-aminobenzyl)-3,8-diazabicyclo[3.2.1]octane, 3-ethyl-3,8-diazabicyclo[3.2.1]octane, 3-benzyl-3,8-diazabicyclo[3.2.1]octane and 2-methyl-2,5-diazabicyclo[2.2.2]octane dihydrochloride.

The compounds of the formula (V) used as starting substances are known. Examples which may be mentioned are: methyl iodide, methyl bromide, ethyl iodide, ethyl bromide, ethyl chloride, 2-hydroxyethyl chloride, 3-hydroxypropyl chloride, 4-hydroxybutyl chloride, n-propyl bromide, i-propyl iodide, n-butyl bromide, i-butyl bromide, sec.-butyl chloride, n-pentyl chloride, 3-methylbutyl chloride, n-hexyl bromide, formic acid-acetic acid anhydride, acetic anhydride, propionic anhydride, acetyl chloride, chloroacetyl chloride, dichloroacetyl chloride, bromoacetyl bromide, butyryl chloride, 4-chlorobutyryl chloride, isobutyryl chloride, N-(tert.-butoxycarbonyl)-glycine 4-nitrophenyl ester, N-(tert.-butoxycarbonyl)-L-alanine 4-nitrophenyl ester, N-(tert.-butoxycarbonyl)-L-leucine 4-nitrophenyl ester, N-(tert.-butoxycarbonyl)-L-valine 4-nitrophenyl ester, 3-methoxypropionyl chloride, methylchlorocarbonate, ethylchlorocarbonate, n-butylchlorocarbonate, diethylcarbonate, cyanogen chloride, diphenylcarbonate, cyanogen bromide, dimethylcarbamoyl chloride, methanesulphonyl chloride, ethanesulphonyl chloride, propane-1-sulphonyl chloride and formic acid.

The compounds of the formula (VII) which can be used according to the invention are known. Examples which may be mentioned are: acrylonitrile, methylvinylketone, methylacrylate and ethylacrylate.

The reaction of (II) with (III) according to Method A is preferably carried out in a diluent, such as dimethyl sulphoxide, N,N-dimethylformamide, hexamethylphosphoric acid trisamide, sulpholane, water, an alcohol, such as methanol, ethanol, N-propanol, isopropanol or glycolmonomethylether, or pyridine. Mixtures of these diluents can also be used.

All the customary organic and inorganic acid-binding agents can be used as the acid-binding agent. These include, preferably, the alkali metal hydroxides, alkali metal carbonates, organic amines and amidines. Specific examples which may be mentioned as particularly suitable are: triethylamine, 1,4-diazabicyclo[2.2.2]octane (DABCO), 1,8-diazabicyclo[5.4.0]undec-7-ene (DBU) or excess amine (III).

The reaction temperatures can be varied within a substantial range. The reaction is in general carried out between about 20° and 200° C., preferably between 80° and 180° C.

The reaction can be carried out under normal pressure or under increased pressure. It is in general carried out under pressures between about 1 and about 100 bar, preferably between 1 and 10 bar.

In carrying out the process according to the invention, 1 to 15 mol, preferably 1 to 6 mol of the amine (III) are employed per mole of the carboxylic acid (II).

The reaction of (IV) with (V) is preferably carried out with a diluent, such as dimethyl sulphoxide, dioxane, N,N-dimethylformamide, hexamethylphosphoric acid trisamide, sulpholane, water, an alcohol, such as methanol, ethanol, n-propanol, isopropanol or glycolmonomethylether, or pyridine. Mixtures of these diluents can also be used.

Acid-binding agents which can be used are all the customary inorganic and organic acid-binding agents. These include, preferably, the alkali metal hydroxides, alkali metal carbonates, organic amides and amidines. Specific examples which may be mentioned as particularly suitable are: triethylamine, 1,4-diazabicyclo[2.2.2]octane (DABCO) or 1,8-diazabicyclo[5.4.0]undec-7ene (DBU).

The reaction temperatures can be varied within a substantial range. The reaction is in general carried out between about 20° and about 180° C., preferably between 40° and 110° C.

The reaction can be carried out under normal pressure, but also under increased pressure. It is in general carried out under pressures between about 1 and about 100 bar, preferably between 1 and 10 bar.

In carrying out the process according to the invention by Method B, 1 to 4 mol, preferably 1 to 1.5 mol, of the compound (V) are employed per 1 mol of the compound (IV).

The reaction of (IV) with (VI) (Method C) is preferably carried out in a diluent, such as dioxane, dimethyl sulphoxide, N,N-dimethylformamide, methanol, ethanol, isopropanol, n-propanol, glycolmonomethylether or mixtures of these diluents.

The reaction temperatures can be varied within a substantial range. The reaction is in general carried out between about 20° C. and about 150° C., preferably between 50° C. and 100° C.

The reaction can be carried out under normal pressure, but also under increased pressure. It is in general carried out under pressures of between about 1 and about 100 bar, preferably between 1 and 10 bar.

In carrying out the process according to the invention by Method C, 1 to 5 mol, preferably 1 to 2 mol, of the compound (VI) are employed per mol of the compound (IV).

New active compounds which may be mentioned specifically, in addition to the compounds mentioned in the examples, are: 8-cyano-1-cyclopropyl-6-fluoro-1,4- dihydro-7-(4-morpholinyl)-4-oxo-3-quinolinecarboxylic acid, 8-cyano-1-cyclopropyl-6-fluoro-1,4-dihydro-4-oxo-7-(3-phenyl-1-piperazinyl)-3-quinolinecarboxylic acid, 6-chloro-8-cyano-1-cyclopropyl-1,4-dihydro-4-oxo-7-(1-piperazinyl)-3-quinolinecarboxylic acid, 8-cyano-1-cyclopropyl-6-fluoro-1,4-dihydro-oxo(4-thiomorpholinyl)-3-quinolinecarboxylic acid, 8-cyano-1-cyclopropyl-6-fluoro-1,4-dihydro-7-(1-piperidinyl)-4-oxo-3-quinolinecarboxylic acid, 7-(3-amino-1-pyrrolidinyl)-8-cyano-1-cyclopropyl-1,4-dihydro-4-oxo-3-quinolinecarboxylic acid, 8-cyano-1-cyclopropyl-6-fluoro-1,4-dihydro-4-oxo-7(1-piperidinyl)-3-quinolinecarboxylic acid, 8-cyano-1-cyclopropyl-7-(3-ethylamino-1-pyrrolidinyl)-6-fluoro-1,4-dihydro-4-oxo-3-quinolinecarboxylic acid, 8-cyano-1-cyclopropyl-7(3-ethylaminomethyl-1-pyrrolidinyl)-6-fluoro-1,4-dihydro-4-oxo-3-quinolinecarboxylic acid, 8-cyano-1-cyclopropyl-7-(2,5-diazabicyclo[2.2.1]oct-5-yl)-6-fluoro-1,4-dihydro-4-oxo-3-quinolinecarboxylic acid, 8-cyano-1-cyclopropyl-7-(3,8-diazabicyclo[3.2.1]oct-3-yl)-6-fluoro-1,4-dihydro-4-oxo-3-quinolinecarboxylic acid, 8-cyano-1-cyclopropyl-6-fluoro-1,4-dihydro-7(5-methyl-2,5-diazabicyclo[2.2.1]hept-2-yl)4-oxo-3-quinolinecarboxylic acid, 6-chloro-8-cyano-1-cyclopropyl-7-(3,8-diazabicyclo[3.2.1]oct-3-yl]-1,4-dihydro-4-oxo-3-quinolinecarboxylic acid, 6-chloro-8-cyano-1-cyclopropyl-1,4-dihydro-7-(5-methyl-2,5-diazabicyclo[2.2.1]-hept-2-yl)-4-oxo-3-quinolinecarboxylic acid, 8-cyano-1-cyclopropyl-1,4-dihydro-7-(5-methyl-2,5-diazabicyclo[2.2.1]hept-2-yl)-6-nitro-4-oxo-3-quinolinecarboxylic acid, 8-cyano-1-cyclopropyl-1,4-dihydro-6-nitro-4-oxo-7(1-piperazinyl)-3-quinolinecarboxylic acid, 8-cyano-1-cyclopropyl-1,4-dihydro-7-(3-methyl-1-piperazinyl)-6-nitro-4-oxo-3-quinolinecarboxylic acid, 8-cyano-1-cyclopropyl-1,4-dihydro-6-nitro-4-oxo-7-(3-phenyl-1-piperazinyl)-3-quinolinecarboxylic acid, 6-(3-amino-1-pyrrolidinyl)-8-cyano-1-cyclopropyl-1,4-dihydro-6-nitro-4-oxo-3-quinolinecarboxylic acid, 8-cyano-1-cyclopropyl-5,6-difluoro-1,4-dihydro-4-oxo-7-(1-piperazinyl)-3-quinolinecarboxylic acid, 8-cyano-1-cyclopropyl-5,6-difluoro-1,4-dihydro-7-(4-methyl-1-piperazinyl)-4-oxo-3-quinolinecarboxylic acid, 5-chloro-8-cyano-1-cyclopropyl-6-fluoro-1,4-dihydro-7-(4-methyl-1-piperazinyl)-4-oxo-3-quinolinecarboxylic acid, 5-chloro-8-cyano-1-cyclopropyl-7-(3,8-diazabicyclo[3.2.1]-oct-3-yl)-6-fluoro-1,4-dihydro-4-oxo-3-quinolinecarboxylic acid, 5-chloro-8-cyano-1-cyclopropyl-7-(3-ethylamino-1-pyrrolidinyl)-6-fluoro-1,4-dihydro-4-oxo-3-quinolinecarboxylic acid, 8-cyano-1-cyclopropyl-6-fluoro-1,4-dihydro-5-methyl-4-oxo-7-(1-piperazinyl)-3-quinolinecarboxylic acid, 7-(3-amino-1-pyrrolidinyl)-8-cyano-1-cyclopropyl-6-fluoro-1,4-dihydro-5-methyl-4-oxo-3-quinolinecarboxylic acid, 8-cyano-1-cyclopropyl-6-fluoro-1,4-dihydro-5-methyl-4-oxo-7-(3-phenyl-1-piperazinyl)-3-quinolinecarboxylic acid, 8cyano-1-cyclopropyl-7-(3,8-diazabicyclo[3.2.1]oct-3-yl)-6-fluoro-1,4-dihydro-5-methyl-4-oxo-3-quinolinecarboxylic acid, 8-cyano-1-cyclopropyl-7-(3-ethylamino-1-pyrrolidinyl)-6-fluoro-1,4-dihydro-5-methyl-4-oxo-3-quinolinecarboxylic acid, 8-cyano-1-cyclopropyl-1,4-dihydro-5,6-dimethyl-4-oxo-7-(1-piperazinyl)-3-quinolinecarboxylic acid, and 8-cyano-1-cyclopropyl-1,4-dihydro-5,6-dimethyl-4-oxo-7-(1-pyrrolidinyl)-3-quinolinecarboxylic acid.

The following examples illustrate the invention.

EXAMPLE 1

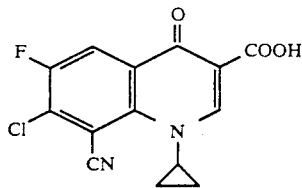

7-Chloro-8-cyano-1-cyclopropyl-6-fluoro-1,4-dihydro-4-oxo-3-quinolinecarboxylic acid.

1.2 g of magnesium filings are stirred into 3 ml of ethanol and 0.3 ml of $CCl_4$ and, when the reaction has started, 7 g of diethylmalonate in 5 ml of EtOH and 18 ml of toluene are added dropwise at 50°-60° C. The mixture is subsequently stirred at this temperature for 1 hour and cooled to −5° to −10° C., a solution of 11 g of 2,4-dichloro-3-cyano-5-fluorobenzoyl chloride in 5 ml of toluene is added dropwise and the mixture is stirred at 0° C. for a further hour and left to stand at room temperature overnight. It is then cooled and 20 ml of water and 3 ml of concentrated $H_2SO_4$ are added. The organic phase is separated off, the aqueous phase is extracted with toluene and the combined organic phases are washed with saturated NaCl solution, dried with sodium sulphate and concentrated.

The residue (16.7 g) is boiled with 20 ml of water and 0.35 g of p-toluenesulphonic acid for 4.5 hours. The mixture is then extracted with $CH_2Cl_2$ and the organic phase is washed with sodium chloride solution, dried over sodium sulphate and concentrated. 11.6 g of residue remain.

The residue is heated at 150° C. together with 8.7 g of orthoformate and 9.8 g of acetic anhydride for two hours and the mixture is subsequently concentrated at 120°-130° C., first under atmospheric pressure and then under a high vacuum. 12.7 g of ethyl 2-(2,4-dichloro-3-cyano-5-fluorobenzoyl)-3-ethoxyacrylate are obtained as an oil.

2.5 g of cyclopropylamine are added to the 12.7 g of this compound in 30 ml of ethanol, while cooling with ice, and the mixture is stirred at room temperature for 2 hours. Thereafter, it is stirred with 30 ml of water and cooled in ice and the solid which has precipitated out is separated off, washed with water and dried.

11.8 g of ethyl 2-(2,4-dichloro-3-cyano-5-fluorobenzoyl)-3-cyclopropylaminoacrylate of melting point 65°-67° C. are obtained.

41.2 g of this compound and 13.6 g of KOtBu are stirred in 500 ml of dioxane at room temperature for 24 hours. Water is then added and the mixture is extracted with $CH_2Cl_2$.

The organic phase is washed, dried over sodium sulphate and concentrated. The residue which remains is stirred with isopropanol. The solid obtained is isolated and dried. 18.0 g of ethyl 7-chloro-8-cyano-1-cyclopropyl-6-fluoro-1,4-dihydro-4-oxo-3-quinolinecarboxylate of melting point 162°-65° C. are obtained.

1 g of this compound is heated at 140°-5° C. together with 3.5 ml of acetic acid, 3 ml of water and 0.3 ml of sulphuric acid for 4 hours. The mixture is then diluted with water and the solid is isolated. 0.7 g of the title compound of melting point 281°-282° C. are obtained.

EXAMPLE 2

8-Cyano-1-cyclopropyl-6-fluoro-1,4-dihydro-4-oxo-7-(1-piperazinyl)-3-quinolinecarboxylic acid

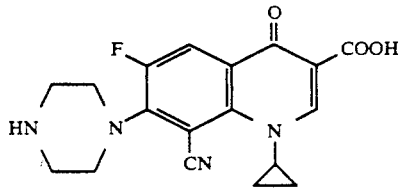

0.5 g of the product from Example 1 and 0.42 g of piperazine are boiled in 8 ml of dioxane for 3 hours. The mixture is then concentrated in vacuo and 8 ml of water are added to the residue. The solution formed is rendered neutral with HCl and the solid which has precipitated out isolated, washed and dried.

Yield: 0.4 g of the title compound
Melting point: >300° C.

EXAMPLE 3

8-Cyano-1-cyclopropyl-6-fluoro-1,4-dihydro-7(4-methyl-1-piperazinyl)-4-oxo-3-quinolinecarboxylic acid

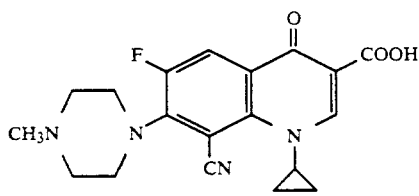

0.5 g of the product from Example 1 and 0.48 g of N-methylpiperazine are boiled in 8 ml of dioxane for 3 hours. The mixture is then concentrated in vacuo, water is added to the residue and the solution formed is rendered neutral. The solid which has precipitated out is isolated, washed and dried.

Yield: 0.5 g of the title compound
Melting point: 264°–265° C.

EXAMPLE 4

8-Cyano-1-cyclopropyl-7-(4-ethyl-1-piperazinyl)-6-fluoro-1,4-dihydro-4-oxo-3-quinolinecarboxylic acid

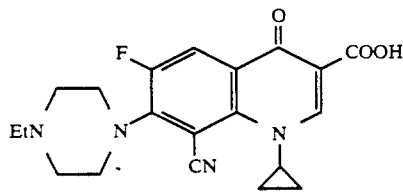

0.5 g of the product from Example 1 and 0.55 g of N-ethylpiperazine are boiled in 8 ml of dioxane for 3 hours. The mixture is then concentrated in vacuo. The residue is taken up in water and rendered neutral. The mixture is extracted with methylene chloride and the organic phase is separated off, dried over sodium sulphate and concentrated. 0.5 g of the title compound of melting point >300° C. remains.

EXAMPLE 5

8-Cyano-1-cyclopropyl-6-fluoro-1,4-dihydro-7-(3-methyl-1-piperazinyl)-4-oxo-3-quinolinecarboxylic acid

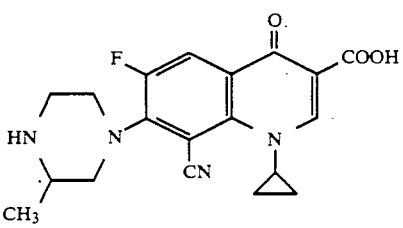

0.5 g of the product from Example 1 and 0.48 g of 2-methylpiperazine are boiled in 8 ml of dioxane for 3 hours. The mixture is then concentrated in vacuo and water is added to the residue.

1N HCl is added until the solution is neutral. The solid which has precipitated out is filtered off with suction and dried. 0.4 g of the title compound with a melting point of >300° C. is obtained.

EXAMPLE 6

8-Cyano-1-cyclopropyl-6-fluoro-1,4-dihydro-4-oxo-7-(1-pyrrolidinyl)-3-quinolinecarboxylic acid

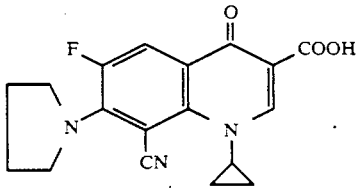

3.05 g of the product from Example 1 and 2.5 ml of pyrrolidine are boiled in 50 ml of dioxane for 3 hours. The mixture is concentrated in vacuo and the residue is taken up in water. The mixture is rendered neutral with 1N HCl. The solid which has precipitated out is filtered off with suction, dried and stirred with acetonitrile. 1.8 g of the title compound with a melting point of 274°–6° C. are obtained.

Example of a tablet according to the invention

Each tablet contains:

| | |
|---|---|
| Compound of Example 5 | 583.0 mg |
| Microcrystalline cellulose | 55.0 mg |
| Maize starch | 72.0 mg |
| Poly-(1-vinyl-2-pyrrolidone) insoluble | 30.0 mg |
| Highly dispersed silicon dioxide | 5.0 mg |
| Magnesium stearate | 5.0 mg |
| | 750.0 mg |

The lacquer shell contains:

| | |
|---|---|
| Poly-(O-hydroxypropyl-O-methyl)-cellulose 15 cp | 6.0 mg |
| Macrogol 4000 recommended INN Polyethyleneglycol (DAB) | 2.0 mg |
| Titanium-(IV) oxide | 2.0 mg |
| | 10.0 mg |

The compounds according to the invention exhibit a broad antibacterial spectrum against Gram-positive and Gram-negative germs, in particular against Enterobacteriaceae-above all against those which are resistant to various antibiotics, such as, for example, penicillins, cephalosporins, aminoglycosides, sulphonamides and tetracyclines-coupled with a low toxicity.

These useful properties enable them to be used as chemotherapeutic active compounds in medicine and as substances for the preservation of inorganic and organic materials, in particular all types of organic materials, for example polymers, lubricants, paints, fibers, leather, paper and wood, and foodstuffs and water.

The compounds according to the invention are active against a very broad spectrum of microorganisms. With the aid of the compounds, Gram-negative and Gram-positive bacteria and bacteria-like microorganisms can be combated and the diseases caused by these pathogens can be prevented, alleviated and/or cured.

The compounds according to the invention are particularly active against bacteria and bacteria-like microorganisms. They are therefore particularly suitable in human and veterinary medicine for the prophylaxis and chemotherapy of local and systemic infections caused by these pathogens.

For example, local and/or systemic diseases which are caused by the following pathogens or by mixtures of the following pathogens can be treated and/or prevented: Gram-positive cocci, for example Staphylococci (*Staph. aureus* and *Staph. epidermidis*) and Streptococci (*Strept. agalactiae, Strept. faecalis, Strept. pneumoniae* and *Strept. pyogenes*); Gram-negative cocci (*Neisseria gonorrhoaea*) and Gram-negative rod-shaped bacilli, such as Enterbacteriaciae, for example *Escherichia coli, Haemophilus influenzae*, Citrobacter (*Citrob. freundii* and *Citrob. divernis*), Salmonella and Shigella; and furthermore Klebsiellae (*Klebs. pneumoniae* and *Klebs. oxytoca*), Enterobacter (*Ent. aerogenes* and *Ent. agglomerans*), Hafnia, Serratia (*Serr. marcescens*), Proteus (*Pr. mirabilis, Pr. rettgeri* and *Pr. vulgaris*), Providencia, Yersinia and the genus Acinetobacter. The antibacterial spectrum moreover includes the genus Pseudomonas (*Ps. aeruginosa* and *Ps. maltophilia*) and strictly anaerobic bacteria, such as, for example, *Bacteroides fragilis*, representatives of the genus Peptococcus, Peptostreptococcus and the genus Clostridium; and furthermore Mycoplasma (*M. pneumoniae, M. hominis* and *M. urealyticum*) and mycobacteria, for example *Mycobacterium tuberculosis*.

The above list of pathogens is purely by way of example and is in no way to be interpreted as limiting. Examples which may be mentioned of diseases which can be caused by the pathogens or mixed infections mentioned and can be prevented, alleviated or cured by the compounds according to the invention are: infectious diseases in humans, such as, for example, otitis, pharyngitis, pneumonia, peritonitis, pyelonephritis, cystitis, endocarditis, systemic infections, bronchitis (acute and chronic), septic infections, diseases of the upper respiratory tract, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmons, wound infections, infected burns, burn wounds, infections in the oral region, infections following dental operations, osteomyelitis, septic arthritis, cholecystitis, peritonitis with appendicitis, cholangitis, intraabdominal abscesses, pancreatitis, sinusitis, mastoiditis, mastitis, tonsillitis, typhus, meningitis and infections of the nervous system, salpingitis, endometritis, genital infections, pelveoperitonitis and eye infections.

Bacterial infections in other species, as well as in humans, can also be treated. Examples which may be mentioned are:

Pigs: coli diarrhoea, enterotoxaemia, sepsis, dysentery, salmonellosis, mastitis-metritis-agalactia syndrome and mastitis;

Ruminants (cattle, sheep, goats): diarrhoea, sepsis, bronchopneumonia, salmonellosis, pasteurellosis, mycoplasmosis and genital infections;

Horses: various types of bronchopneumonia, joint ill, puerperal and post-puerperal infections and salmonellosis;

Dogs and cats: bronchopneumonia, diarrhoea, dermatitis, otitis, urinary tract infections and prostatitis; and Poultry (chickens, turkeys, quail, pigeons, ornamental birds and others): mycoplasmosis, *E. coli* infections, chronic respiratory tract infections, salmonellosis, pasteurellosis and psittacosis.

Bacterial diseases can also be treated in the breeding and rearing of useful and ornamental fish, the antibacterial spectrum extending beyond the abovementioned pathogens to further pathogens, such as, for example, Pasteurella, Brucella, Campylobacter, Listeria, Erysipelothrix, Corynebacteria, Borrelia, Treponema, Nocardia, Rickettsia and Yersinia.

The present invention includes pharmaceutical formulations which, in addition to non-toxic inert pharmaceutically suitable excipients, contain one or more compounds according to the invention or consist of one or more active compounds according to the invention, and processes for the preparation of these formulations.

The present invention also includes pharmaceutical formulations in dosage units. This means that the formulations are present in the form of individual parts, for example tablets, dragees, capsules, pills, suppositories and ampoules, the active compound content of which corresponds to a fraction or a multiple of an individual dose. The dosage units can contain, for example, 1, 2, 3 or 4 individual doses or a ½, a ⅓ or a ¼ of an individual dose. An individual dose preferably contains the amount of active compound which is given in one administration and usually corresponds to a whole, one half, one third or one quarter of a daily dose.

By non-toxic inert pharmaceutically suitable excipients there are to be understood all types of solid, semi-solid or liquid diluents, fillers and formulation auxiliaries.

Preferred pharmaceutical formulations which may be mentioned are tablets, dragees, capsules, pills, granules, suppositories, solutions, suspensions and emulsions, pastes, ointments, gels, creams lotions, powders and sprays.

Tablets, dragees, capsules, pills and granules can contain the active compound or compounds, in addition to the customary excipients, such as (a) fillers and extenders, for example starches, lactose, sucrose, glucose, mannitol and silicic acid, (b) binders, for example carboxymethylcellulose, alginates, gelatins and polyvinylpyrrolidone, (c) humectants, for example glycerol, (d) disintegrating agents, for example agar-agar, calcium carbonate and sodium carbonate, (e) solution retarders, for example paraffin, and (f) absorption accelerators, for example quaternary ammonium compounds, (g) wetting agents, for example cetyl alcohol and glycerol monostearate, (h) adsorbents, for example kaolin and bentonite, and (i) lubricants, for example talc, calcium stearate and magnesium stearate and solid polyethyleneglycols or mixtures of the substances listed under (a) to (i).

The tablets, dragees, capsules, pills and granules can be provided with the customary coatings and shells, optionally containing opacifying agents, and can also be of such composition that they release the active compound or compounds only or preferentially in a certain part of the intestinal tract, if appropriate in a delayed manner, examples of embedding compositions which can be used being polymeric substances and waxes.

The active compound or compounds can also be in microencapsulated form, if appropriate with one or more of the abovementioned excipients.

Suppositories can contain, in addition to the active compound or compounds, the customary water-soluble or water-insoluble excipients, for example polyethylene glycols, fats, for example cacao fat, and higher esters (for example $C_{14}$-alcohol with $C_{16}$-fatty acid), or mixtures of these substances.

Ointments, pastes, creams and gels can contain, in addition to the active compound or compounds, the customary excipients, for example animal and vegetable fats, waxes, paraffins, starch, tragacanth, cellulose derivatives, polyethyleneglycols, silicones, bentonites, silicic acid, talc and zinc oxide, or mixtures of these substances.

Powders and sprays can contain, in addition to the active compound or compounds, the customary excipients, for example lactose, talc, silicic acid, aluminium hydroxide, calcium silicate and polyamide powder, or mixtures of these substances. Sprays can additionally contain the customary propellants, for example chlorofluorohydrocarbons.

Solutions and emulsions can contain, in addition to the active compound or compounds, the customary excipients, such as solvents, solubilizing agents and emulsifiers, for example water, ethyl alcohol, isopropyl alcohol, ethylcarbonate, ethylacetate, benzyl alcohol, benzyl benzoate, propylene glycol, 1,3-butylene glycol, dimethylformamide, oils, in particular cotton seed oil, groundnut oil, maize germ oil, olive oil, castor oil and sesame oil, glycerol, glycerol formal, tetrahydrofurfuryl alcohol, polyethylene glycol and fatty acid esters of sorbitan, or mixtures of these substances.

For parenteral administration, the solutions and emulsions can also be in a sterile form which is isotonic with blood.

Suspensions can contain, in addition to the active compound or compounds, the customary excipients, such as liquid diluents, for example water, ethyl alcohol or propylene glycol, suspending agents, for example ethoxylated isostearyl alcohols, polyoxyethylene sorbitol and sorbitan esters, microcrystalline cellulose, aluminum methahydroxide, bentonite, agar-agar and tragacanth, or mixtures of these substances.

The formulation forms mentioned can also contain coloring agents, preservatives and additives which improve the smell and taste, for example peppermint oil and eucalyptus oil, and sweeteners, for example saccharin.

The therapeutically active compounds should preferably be present in the abovementioned pharmaceutical formulations in a concentration of about 0.1 to 99.5, preferably about 0.5 to 95% by weight of the total mixture.

In addition to the compounds according to the invention, the abovementioned pharmaceutical formulations can also contain other pharmaceutical active compounds.

The abovementioned pharmaceutical formulations are prepared in a customary manner by known methods, for example by mixing the active compound or compounds with the excipient or excipients.

The formulations mentioned can be administered to humans and animals either orally, rectally, parenterally (intravenously, intramuscularly or subcutaneously), intracisternally, intravaginally, intraperitoneally or locally (powders, ointments and drops) and for the therapy of infections in hollow spaces and body cavities. Suitable formulations are injection solutions, solutions and suspensions for oral therapy and gels, infusion formulations, emulsions, ointments or drops. Ophthalmological and dermatological formulations, silver salts and other salts, ear drops, eye ointments, powders or solutions can be used for local therapy. In the case of animals, intake can also be via the feed or drinking water in suitable formulations. It is furthermore possible to use gels, powders, dusting agents, tablets, sustained release tablets, premixes, concentrates, granules, pellets, boli, capsules, aerosols, sprays and inhalates on humans and animals. The compounds according to the invention can furthermore be incorporated into other carrier materials, such as, for example, plastics (chains of plastics for local therapy), collagen or bone cement.

In general, it has proved advantageous both in human and in veterinary medicine to administer the active compound or compounds according to the invention in total amounts of about 0.5 to about 500, preferably 5 to 100 mg/kg of body weight every 24 hours, if appropriate in the form of several individual doses, in order to achieve the desired results. An individual dose preferably contains the active compound or compounds according to the invention in amounts of about 1 to about 80, in particular 3 to 30 mg/kg of body weight. However, it may be necessary to deviate from the dosages mentioned, and in particular to do so as a function of the nature and body weight of the subject to be treated, the nature and severity of the disease, the nature of the formulation and of the administration of the medicament and the period or interval within which administration takes place.

Thus in some cases it may suffice to manage with less than the abovementioned amount of active compound, whilst in other cases the abovementioned amount of active compound must be exceeded. The particular optimum dosage and mode of administration required for the active compounds can easily be determined by any expert on the basis of his specialist knowledge.

The new compounds can be administered together with the feed or with feed formulations or with the drinking water in the customary concentrations and formulations. An infection by Gram-negative or Gram-positive bacteria can thereby be prevented, alleviated and/or cured and a promotion in growth and an improvement in feed utilization can thereby be achieved.

What is claimed is:

1. An 8-cyano-1-cyclopropyl-1,4-dihydro-4-oxo-3-quinolinecarboxylic acid derivative of the formula

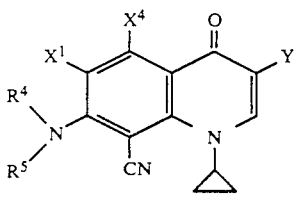

in which
Y represents carboxyl, nitrile, —COOR¹—CONR² R³, wherein
R¹ represents alkyl, and
R² and R³ each independently represent hydrogen or alkyl, and
R³ represents an unsubstituted or substituted phenyl,
X¹ represents hydrogen, nitro, alkyl, or halogen,
X⁴ represents hydrogen or halogen or alkyl,
R⁴ and R⁵, together with the nitrogen atom to which they are bonded, form a 6-membered heterocyclic ring which additionally have the atoms or groups —S—, —SO—, or —SO₂—, as a ring member and which is unsubstituted or mono-, di- or trisubstituted on the carbon atoms by identical or different substituents said substituents being $C_1$-$C_4$-alkyl, phenyl and cyclohexyl and said substituents being unsubstituted or mono-, di- or trisubstituted by chlorine, fluorine, bromine, methyl, phenyl, hydroxyl, methoxy, benzyloxy, nitro or piperidino, 2-thienyl, hydroxyl, alkoxy with one to three carbon atoms, amino, methylamino, ethylamino, aminomethyl, methylaminomethyl and ethylaminomethyl; pharmaceutically acceptable hydrates or salts thereof, and their esters.

2. A compound according to claim 1, wherein
R¹ represents $C_1$-$C_4$-alkyl and
R² and R³ each independently represent hydrogen or $C_1$-$C_4$-alkyl,
X¹ represents hydrogen, nitro, $C_1$-$C_3$-alkyl or halogen,
X⁴ represents hydrogen or halogen or $C_1$-$C_3$-alkyl.

3. A compound according to claim 1 which is 8-cyano-1-cyclopropyl-6-fluoro-1,4-dihydro-4-oxo-7-(4-thiomorpholinyl)-3-quinoline carboxylic acid.

4. An antibacterial composition comprising an antibacterially effective amount of a compound according to claim 1 and a pharmaceutically acceptable excipient.

5. A unit dosage form of a composition according to claim 4.

6. A method of combating bacteria which comprises administering to a patent in need thereof an effective amount of a compound according to claim 1.

* * * * *